(12) United States Patent
Curtin et al.

(10) Patent No.: US 11,517,210 B2
(45) Date of Patent: Dec. 6, 2022

(54) NON-INVASIVE BLOOD PRESSURE MEASUREMENT

(71) Applicant: Physio-Control, Inc., Redmond, WA (US)

(72) Inventors: Barry Curtin, Redmond, WA (US); Matthew L. Bielstein, Redmond, WA (US)

(73) Assignee: Physio-Control, Inc., Redmond, WA (US)

(*) Notice: Subject to any disclaimer, the term of this patent is extended or adjusted under 35 U.S.C. 154(b) by 517 days.

(21) Appl. No.: 16/334,328

(22) PCT Filed: Sep. 27, 2017

(86) PCT No.: PCT/US2017/053809
§ 371 (c)(1),
(2) Date: Mar. 18, 2019

(87) PCT Pub. No.: WO2018/064217
PCT Pub. Date: Apr. 5, 2018

(65) Prior Publication Data
US 2019/0209032 A1   Jul. 11, 2019

Related U.S. Application Data

(60) Provisional application No. 62/401,707, filed on Sep. 29, 2016.

(51) Int. Cl.
*A61B 5/022* (2006.01)
*A61B 8/00* (2006.01)
(Continued)

(52) U.S. Cl.
CPC ...... *A61B 5/02225* (2013.01); *A61B 5/02233* (2013.01); *A61B 8/4227* (2013.01); *A61B 5/026* (2013.01); *A61B 5/6824* (2013.01)

(58) Field of Classification Search
CPC ... A61B 5/4227; A61B 5/6824; A61B 5/7203; A61B 5/02225
See application file for complete search history.

(56) References Cited

U.S. PATENT DOCUMENTS 3,156,237 A   11/1964   Edmark
4,726,382 A    2/1988   Boehmer et al.
(Continued)

FOREIGN PATENT DOCUMENTS

WO   WO-2014121945 A1 * 8/2014   ......... A61B 5/02233

OTHER PUBLICATIONS

International Search Report and Written Opinion dated Nov. 27, 2017, International Application No. PCT/US2017/053809, Intentional Filing Date Sep. 27, 2017.
(Continued)

*Primary Examiner* — Jay B Shah
(74) *Attorney, Agent, or Firm* — Lee & Hayes, P.C.

(57) ABSTRACT

A non-invasive blood pressure (NIBP) measurement system that includes a blood pressure cuff and a non-invasive blood pressure monitor. The blood pressure cuff including an inner portion that is selectively inflatable and an outer portion that is rigid or semi-rigid. The outer portion reducing external stimuli on the inner portion. The inner portion connected to a sensor coupled to the NIBP monitor, the sensor sensing a pressure of the inner portion. The NIBP monitor receiving the sensor data and processing the sensor data to determine a blood pressure of a patient about which the blood pressure cuff has been placed.

20 Claims, 6 Drawing Sheets

(51) Int. Cl.
  *A61B 5/026* (2006.01)
  *A61B 5/00* (2006.01)

(56) References Cited

U.S. PATENT DOCUMENTS

| | | | |
|---|---|---|---|
| 4,790,325 A | 12/1988 | Lee | |
| 5,660,182 A | 8/1997 | Kuroshaki et al. | |
| 6,224,558 B1 | 5/2001 | Clemmons | |
| 2001/0000577 A1 | 6/2001 | Nakagawa et al. | |
| 2001/0005777 A1 | 6/2001 | Nakagawa et al. | |
| 2006/0253041 A1* | 11/2006 | Shin | A61B 5/02233 600/493 |
| 2011/0152700 A1* | 6/2011 | Sawanoi | A61B 5/7221 600/493 |
| 2011/0213256 A1* | 9/2011 | Taniguchi | A61B 5/02233 600/493 |
| 2012/0209129 A1 | 8/2012 | Smith et al. | |
| 2012/0302901 A1* | 11/2012 | Kobayashi | A61B 5/02233 600/494 |
| 2013/0060153 A1* | 3/2013 | Kobayashi | A61B 5/02225 600/499 |
| 2015/0366474 A1 | 12/2015 | Pearson et al. | |

OTHER PUBLICATIONS

International Preliminary Report on Patentability dated Apr. 2, 2019, International Application No. PCT/US2017/053809, Intentional Filing Date Sep. 27, 2017.

* cited by examiner

NON-INVASIVE BLOOD PRESSURE MEASUREMENT

CROSS-REFERENCE TO RELATED APPLICATIONS

This application is a 371 filing of international patent application No. PCT/US2017/053809, filed Sep. 27, 2017, which claims the benefit of U.S. Provisional Patent Application Ser. No. 62/401,707, filed Sep. 29, 2016, the contents of which are herein incorporated by reference in their entirety.

BACKGROUND

An accurate measurement of a patient's blood pressure is a vital tool in treating and monitoring the health of a patient. The measurement of a patient's blood pressure can be obtained using invasive and non-invasive methods. Invasive blood pressure measurements involves inserting a physical sensor within the patient's body, such as within an artery, to obtain a direct measurement of the blood pressure of the patient. Non-invasive measurement of a patient's blood pressure can be obtained without the insertion of a sensor, or other equipment, within the patient and typically involve measuring the patient's blood pressure through devices and/or sensors placed on the patient's body, such as the patient's arm or leg. Such non-invasive measurement techniques are typically more comfortable for the patient and are easier and quicker for staff or treatment providers to perform.

Currently, two main forms of non-invasive blood pressure (NIBP) measurement are employed—auscultatory methods and oscillometric methods. Auscultatory methods are performed using an inflatable cuff, a stethoscope, and a sphygmomanometer. A properly trained individual places the cuff on the patient and inflates the cuff to occlude an artery by applying an external pressure via the cuff, until blood flow through the artery is stopped. Then, using the stethoscope, the individual listens for specific noises indicative of the restoration of flow as pressure on the artery is slowly released and noting at which pressures certain noises occur.

Oscillometric methods typically use a digital meter that is connected to an inflatable cuff to obtain measurements and calculate a value of the patient's blood pressure. The cuff is inflated to cause occlusion of an artery and then deflated over a pre-determined period of time until normal flow through the artery is restored. During the pre-determined deflation period, a pressure transducer or other sensor detects and measures pulsing through the artery, i.e. cuff pressure oscillations caused by the artery expanding and contracting. Using the sensed oscillometric waveform, the digital meter can calculate the various components of the patient's blood pressure, such as the systolic, diastolic and mean arterial pressures.

A benefit of a NIBP device that employs the oscillometric method is that there is a reduced level of training and/or skill required of a user in order to effectively use the device to obtain a patient's blood pressure measurement. However, there are also potential drawbacks to using such a device. Due to the oscillometric monitoring of the patient's artery, there is a potential for external sources to influence or affect the signal detected by the pressure transducer or other sensor, which can result in incorrect blood pressure calculations or prevent the calculation of a blood pressure based on the obtained signal. For example, during the pre-determined deflation period, a patient's movement can cause external pressure on the cuff that can be registered by the transducer or sensor which affects the oscillometric waveform that is used to calculate the patient's blood pressure.

Conventional NIBP devices also tend to take too long to inflate in time-critical, emergency situations. Patients suffering from cardiac emergencies often move uncontrollably, shake, seize, or otherwise experience uncontrolled movements that cause inconsistent, incomprehensible, and/or noisy results and require the emergency rescuers to reposition the cuff on the patient's arm. When such a repositioning is required, the rescuers must deflate the cuff entirely before it is inflated. Obtaining a patient's blood pressure during a cardiac emergency is essential to performing lifesaving therapies. The time required to deflate and re-inflate the cuff distracts the rescuers from performing other high-value tasks to help save the patient's life.

It would be desirable to have portable, user-friendly blood pressure measurement systems that have increased accuracy and/or efficiency in obtaining a blood pressure measurement using an oscillometric method. It would also be desirable to have a NIBP device that deflates and re-inflates faster than conventional NIBP devices to save critical time during lifesaving treatment.

SUMMARY

Figure 1:
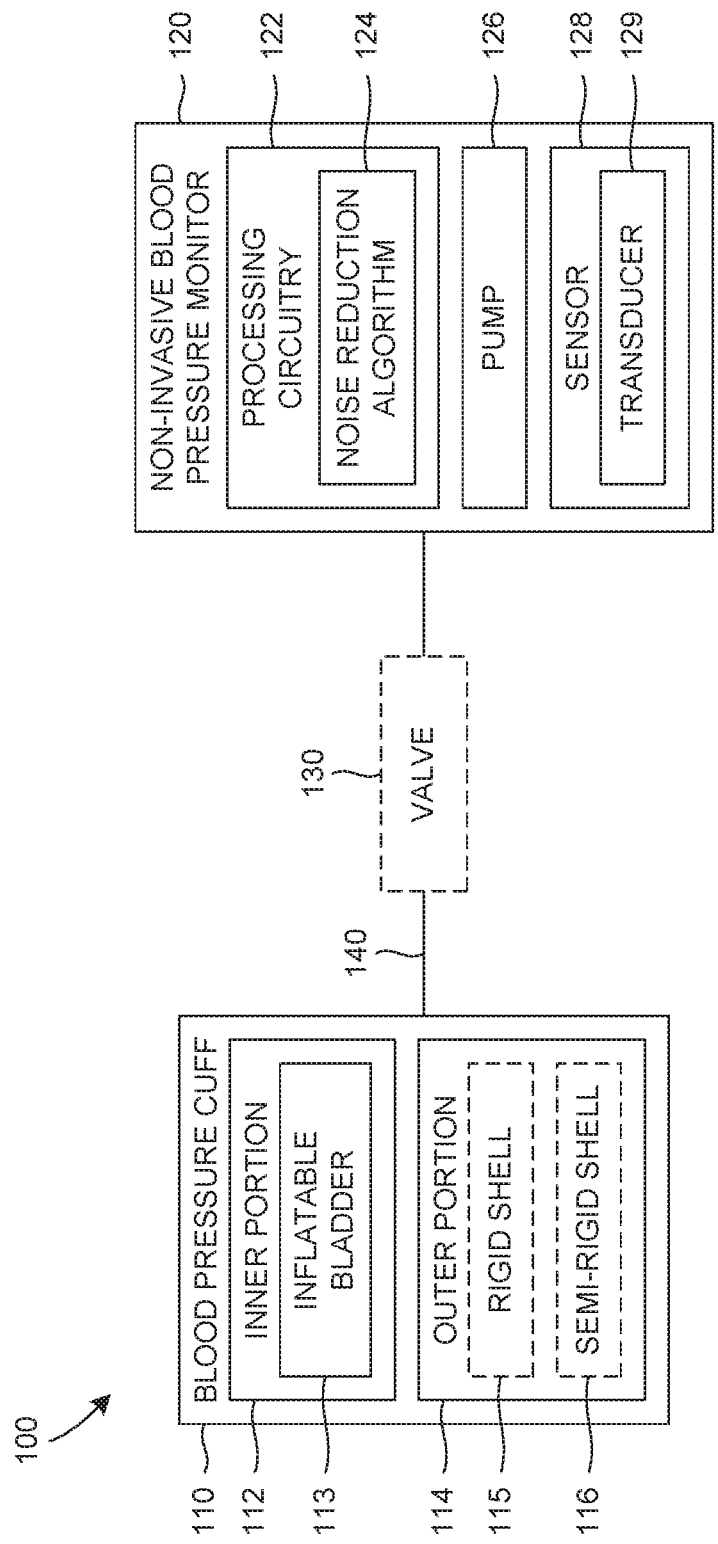
FIG. 1 is a block diagram of an example non-invasive blood pressure measurement system.

An example non-invasive blood pressure measurement system, can include a blood pressure cuff that includes an outer portion that encircles at least some of an inner portion of a blood pressure cuff. The blood pressure cuff, and the inner portion thereof, being structured to fit about at least a portion of a patient, such as an arm. The inner portion also being selectively inflatable. A transducer can be coupled a non-invasive blood pressure monitor and to the inner portion of the blood pressure cuff. The transducer can be configured to sense a pressure of the selectively inflatable portion and output a pressure signal. Processing circuitry of the non-invasive blood pressure monitor can be configured to receive the pressure signal from the transducer and to process the pressure signal to determine a blood pressure of the patient.

In an example embodiment, the outer portion of the blood pressure cuff can include a rigid shell. The rigid shell can be a substantially continuous tube that is sized to fit about the inner portion of the blood pressure cuff. In a further example embodiment, the rigid shell can be formed of two portions that are joined along at least an edge. In yet a further example embodiment, the rigid shell can be formed of two separable portions.

In another example embodiment, the outer portion of the blood pressure cuff can include a semi-rigid shell. The semi-rigid shell can be formed of a multi-layer construction that is secured together to form the semi-rigid shell. In a further example embodiment, the multi-layer construction of the semi-rigid shell can include a fabric. Additionally, the semi-rigid shell can be composed of two, separable portions, with the first portion being substantially flexible and the second portion being substantially rigid. Further, the first portion of the semi-rigid shell can include a pocket for selectively receiving the second portion of the semi-rigid shell.

In a further example embodiment, the outer portion and the inner portion of the blood pressure cuff can be integrated together and the outer portion can be selectively inflatable such that the outer portion becomes at least semi-rigid. In another example embodiment, the outer portion can be at least foldable or collapsible.

In yet a further example embodiment, the transducer can be integrated with the non-invasive blood pressure monitor and the blood pressure cuff can be coupled to the transducer through the blood pressure monitor. Both the blood pressure cuff and the non-invasive blood pressure monitor can be portable and can be selectively coupled together through a tube.

In another example embodiment, a bleed valve can be coupled between the blood pressure cuff and the transducer. The bleed valve can be in fluid communication with the inner portion of the blood pressure cuff and can be structured to selectively actuate to cause at least a portion of a pressure within the inner portion to be released.

A further example non-invasive blood pressure measurement system can include, a cuff that has a selectively inflatable inner portion and an outer portion that is sized to fit the selectively inflatable inner portion. A sensor can be coupled to the cuff and can be configured to output at least a signal indicative of a pressure within the selectively inflatable inner portion. A non-invasive blood pressure monitor can include a pump in fluid communication with the inflatable inner portion of the cuff and processing circuitry that is configured to receive the signal from the sensor. The processing circuitry can include a noise reduction algorithm that can be applied to the received signal to create a reduced noise signal and the processing circuitry can generate an output that includes at least a blood pressure based on the reduced noise signal.

As previously discussed above, the outer portion of the further example blood pressure measurement system can be a rigid shell in an example embodiment or can be a semi-rigid shell in a further example embodiment. In yet a further embodiment, the outer portion can be selectively inflatable and the outer portion can be inflated to a pressure greater than a pressure within the selectively inflatable inner portion of the cuff. Additionally, the outer portion can be formed of at least two elements that are selectively coupled along at least a first portion to form the outer portion of the cuff.

In a further example embodiment, the outer portion can be semi-rigid and formed of at least two elements, with the first element being substantially flexible and the second element being substantially semi-rigid. The two elements can be selectively coupled together to form the outer portion.

DETAILED DESCRIPTION

The invention described herein, provides improved methods and systems for non-invasively measuring blood pressure of a patient. The described non-invasive blood pressure (NIBP) measurement system includes an outer portion that protects an inflatable cuff from external stimuli, such as movements and/or impacts, which might otherwise cause unwanted noise in the signal transmitted by a pressure transducer. An NIBP monitor receives the signal from the pressure transducer and filters out the induced noise to accurately determine a blood pressure of the patient. In some examples, the induced noise caused by the external stimuli can be so great that the NIBP monitor is incapable of properly filtering the signal to calculate the blood pressure. In emergency situations, where an accurate blood pressure can be critical, the chaos and external stimuli of the situation can cause the acquisition of the patient's blood pressure using a NIBP system to take an extended period of time and/or be inaccurate. The outer portion of the disclosed invention protects the inflatable cuff to reduce the effects the external stimuli have on the signal generated by the pressure transducer. This reduced noise signal can be more easily filterable and/or can assist with a more accurate calculation of a blood pressure using an NIBP system. Additionally, the outer portion can constrain the expansion of an inflatable cuff, or inner portion, which can reduce the time required to reach a desired, or required, pressurization of the inflatable cuff.

FIG. 1 illustrates an example non-invasive blood pressure measurement system 100 that includes a blood pressure cuff 110 connected to a non-invasive blood pressure (NIBP) monitor 120 and, optionally, a valve 130 disposed in-between. A tube 140 can link the blood pressure cuff 110 to the NIBP monitor 120 to allow the oscillometric pressure pulse signal to be transmitted from the cuff 110 to a pressure transducer 128, and/or other sensor, of the NIBP monitor 120. While the optional valve 130 is shown in-line with the tube 140 in the example embodiment of FIG. 1, the valve 130 can be separate from and fluidically connected to the tube 140.

The blood pressure cuff 110 can include an inner portion 112, which contacts the patient, and an outer portion 114, that is exposed to the surrounding environment. The inner portion 112, or portion thereof, can be selectively inflatable, such as by an inflatable bladder 113 that can be filled with a gas, such as atmospheric air, to exert pressure on a brachial artery of the patient for which a blood pressure measurement is to be obtained. The pressure exerted by the inflatable bladder 113 on the brachial artery causes the artery to occlude and temporarily stops blood flow through the artery. Various measurements and data can be obtained as the inflatable bladder 113 is deflated over a period of time until normal flow through the artery is resumed. The inflation and deflation of the inflatable bladder 113 can be performed automatically, such as by the NIBP monitor 120, manually, or a combination thereof. As blood flow through the artery is restored, by the controlled release of pressure exerted on the brachial artery by the inflatable bladder 113, the cyclical expansion and contraction of the artery exerts a pulsed pressure on the inflatable bladder 113. These pressure pulses can be transmitted from the blood pressure cuff 110, through the tube 140, to the NIBP monitor 120. The obtained oscillometric waveform of the controlled decreasing pressure of the inflatable bladder 113 and the pressure pulses caused by the expansion and contraction of the brachial artery can be analyzed by the NIBP monitor 120 to determine a blood pressure of the patient. Alternative means of exerting a controlled pressure on the brachial artery to cause occlusion can also be used, such as the tightening of a material about the patient arm or other means of controlled and/or even application to and removal of pressure from the brachial artery.

The outer portion 114 of the blood pressure cuff 110 can minimize the external environmental effects on the inner portion 112 to assist with obtaining a blood pressure measurement. As discussed above, external pressures or forces applied to the inner portion can cause errors or noise in the oscillometric waveform. Such noise can cause errors in the calculated blood pressure of the patient and/or cause so much noise or error that such a calculation cannot be performed. The outer portion 114 protects the inner portion 112 from such external factors to increase the quality and/or accuracy of the obtained oscillometric waveform.

The outer portion 114 can be separate from or integrated with the inner portion 112. When separate from the inner portion 112, the outer portion 114 can be applied about the inner portion 112 prior to obtaining the blood pressure measurement. The outer portion 114 can be a single unit or piece or can be constructed from multiple units or pieces that can be fit together prior to being placed about the inner portion 112 or can be constructed about the inner portion 112. In the multi-piece embodiment, the various components of the outer portion 114 can be connected together or separate to achieve the desired protection of the inner portion 112 from the external environment. The outer portion 114 can constrain an inner portion 112, such as by limiting the expansion of the inflatable bladder 113. The outer portion 114 can have a pre-determined or pre-selected inner circumference, which sets a gap between the outer portion 114 and an unexpanded/uninflated inner portion 112 and limits the expansion/inflation of the inner portion 112 to the inner circumference of the outer portion 114.

An example outer portion 114 can include a rigid shell 115. The rigid shell 115 can be substantially inflexible and resilient to applied external forces, such pressure applied to the blood pressure cuff 110 caused by patient movement, to prevent transmission of the applied external forces to the inner portion 112. The applied external forces can be transmitted through the rigid shell 115 about the inner portion 112 to assist with obtaining the required oscillometric waveform for use in determining a blood pressure of the patient. The rigid shell 115 can be solid piece, such as a tube that is slid over the inner portion 112, or can be constructed of multiple pieces that can be assembled about the inner portion 112. Additionally, the rigid shell 115 can have various portions shaped and/or cut-out, such as a latticework, to reduce the weight of the rigid shell 115 and/or the amount of material required to construct the rigid shell 115.

The rigid shell 115 can be composed of a variety of materials and/or material combinations including fiberglass, plastic, metal, composites and/or other suitable materials. Material selection can be based on a variety of factors, including the desired strength of the rigid shell 115, the cost of manufacturing, ease of manufacturing, storage of the rigid shell 115, expected lifespan/durability of the rigid shell 115, reusability and/or other factors. In another embodiment, the rigid shell 115 can be constructed as a spiral, such that a portion of the rigid shell 115 can wrap around and overlap another portion of the rigid shell 115. This overlap can allow the rigid shell 115 to be adjustable to fit about various circumferences, such as differently sized patient arms and/or inner portions 112 of the blood pressure cuff 110. The adjustable rigid shell 115 can be placed and secured about the inner portion 112 to reduce the effect of external stimuli and/or constrain the inflatable bladder 113 of the inner portion 112 to assist with reducing the inflation time of the inflatable bladder 113. Various securement means can be used to constrain the rigid shell 115 about the inner portion, the securement means can be integrated with the rigid shell 115 or can be separately applied on or about the rigid shell 115.

Another example outer portion 114 can include a semi-rigid shell 116. The semi-rigid shell 116 can exhibit some degree of flexibility while still protecting the inner portion 112 from the external environment. While external forces may be transmitted through the semi-rigid shell 116 to the inner portion 113, the magnitude of the forces transmitted can be reduced to an amount less than otherwise would be imparted on the inner portion 112 without the semi-rigid shell 116 disposed about. An example semi-rigid shell 116 can be constructed of heavy fabrics that are sewn together to form the semi-rigid shell 116. Both the rigid 115 and semi-rigid shell 116 can be constructed such that they are fully or partially collapsible for easy storage of the outer portion 114 when not in use. In the example semi-rigid shell 116 constructed of fabrics and/or other flexible materials, the outer portion 114 can be folded and/or compacted for storage when not in use about a patient.

A further example outer portion 114 can include a semi-rigid shell 116 that is inflatable. The semi-rigid shell 116 can be inflated to a pressure, such as a pressure greater than the pressure to which the inflatable bladder is pressurized, such that the semi-rigid shell 116 has a degree of rigidity due to the inflated nature. Once the semi-rigid shell 116 has been inflated to the necessary pressure, the inflatable bladder 113 of the inner portion 112 can be inflated to begin the acquisition process for obtaining the necessary measurements/data to calculate a patient's blood pressure using the oscillometric method. The pressure to which the semi-rigid shell 116 is inflated can vary and/or can be adjustable either automatically or manually.

The outer portion 114 can be constructed of materials and/or in a manner, such that the physical properties the outer portion 114 exhibits vary. For example, the outer portion 114 can be constructed of materials and/or in a manner such that a tensile strength of the outer portion along a first direction has a first value and the tensile strength of the outer portion along a second direction has a second value. In this manner, the outer portion 114 can exhibit different magnitudes of a physical property based on the material and/or construction used to form the outer portion 114. This can allow an outer portion 114 to be constructed to resist radial expansion, i.e. constrain the inflatable bladder 113 to reduce inflation time, while having axial flexibility to assist with sliding and/or positioning the outer portion 114 about the inner portion 112.

Other materials, such as reactive materials, can be used to form the outer portion 114. Reactive materials can exhibit changed or different material properties in response to an applied stimulus. For example, certain materials may stiffen and/or strengthen in response to an applied stimulus such as an impact or an applied voltage. These materials can be incorporated in the outer portion 114 to assist with obtaining a rigidity for use in restraining the inner portion 112 and reducing the transmission of external forces through the outer portion 114 and into the inner portion 112

The blood pressure cuff 110 is portable, that is, a rescuer can remove and place the cuff about one or more portions of the patient, as needed, i.e. it can be placed on either arm or leg of the patient, and can also be moved easily with a rescuer or placed in an emergency vehicle like an ambulance, helicopter, or other pre-hospital or emergency treatment environment, whether or not in a vehicle. The portability of the disclosed blood pressure cuff 110 is important because it allows the rescuer(s) to transport the device directly to the point-of-care for the patient and easily move the device with the patient during transport of the patient, such as trauma treatment that occurs during emergency transport. Further, the device is also useful in helping to measure a patient's blood pressure when the patient is moving or unable to control physical movement, such as muscle spasms, shivering, and/or tremors that a patient might experience during treatment for a trauma event regardless of whether the patient is stationary or in transport. Additionally, the blood pressure cuff 110 can be reusable, i.e. used multiple times on the same or different patients. The separate and portable nature of both the blood pressure cuff 110 and the NIBP monitor 120 allows the two elements of the NIBP measurement system 100 to be positioned as desired or necessary, such as for storage or use. The two are linked by the tube 140 which extends between the blood pressure cuff 110 and the NIBP monitor 120 to assist with acquisition of the oscillometric signals. Additionally, with the signal noise reducing capabilities of the outer portion 114, repositioning of one or more of the blood pressure cuff 110 and/or the NIBP monitor 120 can be allowed with minimal impact during the acquisition and/or calculation of a blood pressure measurement of the patient.

In addition to reducing external influences on the inner portion 112, the outer portion 114 can assist with the blood pressure measurement by constraining the inner portion 112 against the patient's arm, for example, to reduce the time required to inflate the inflatable bladder to a necessary pressure. As previously discussed, the acquisition of the blood pressure data can start with the occlusion of the brachial, or other, artery of the patient. To occlude the brachial artery, the inflatable bladder 113 is inflated to exert a pressure on the brachial artery, and the inflation continues until a known pressure is reached. At the known pressure, it is preferred that the brachial artery is occluded by the pressure exerted by the inflated inflatable bladder 113. In an unconstrained embodiment, as the inflatable bladder 113 is inflated, it expands both inwardly towards the patient's arm and outward towards the external environment. In a constrained embodiment, such as when the inner portion 112 is at least partially encircled by the outer portion 114, the expanding inflatable bladder 113 is constrained by the outer portion 114. The reduced area of expansion available for the inflatable bladder 113 to expand allows the known pressure of the inflatable bladder 113 to be reached in a shorter time period than otherwise in the unconstrained environment. This reduced inflation time can allow for a reduced overall time required to acquire the necessary measurements/data required to calculate the blood pressure of the patient. The lower overall blood pressure measurement time can reduce the impact of artery occlusion on the patient and patient discomfort.

In emergency situation, the accurate and efficient determination of a patient's blood pressure can be critical to the assessment and/or treatment of the patient. For many patients in an emergency situation, one of the first locations they begin being assessed and treated is in an ambulance or other transport vehicle. During transport, there is a focus on limiting the amount of time it takes to deliver the patient to a hospital or other treatment location where they can be better assessed and/or treated. Further, patients experiencing significant trauma are unlikely to be able to control their limbs from moving due to tremors, seizures, shivering, and the like the patient suffers as a result of the trauma event. Due to the noise of the transport, patient movement, and other factors, the traditional means of using a sphygmomanometer to assess the blood pressure of the patient is often not possible and instead there is an increasing reliance on the use of NIBP measurement systems and techniques.

As discussed previously, NIBP measurement systems, such as 100 of FIG. 1, can be susceptible to noise induced in the oscillometric signal which can reduce the accuracy of or prevent the determination of the patient's blood pressure using an NIBP measurement system. During patient transport the sources and/or magnitudes of external stimuli can be increased due to the dynamic nature of transporting the patient. The increased magnitude and/or sources of external stimuli during transport can further complicate the use of NIBP measurement systems. However, the outer portion 114, described herein, can reduce and/or minimize the noise induced by the external stimuli of a patient transport situation to increase the accuracy and/or efficacy of measuring the patient's blood pressure using the NIBP measurement system 100 of FIG. 1.

The non-invasive blood pressure (NIBP) monitor 120 is connected to the blood pressure cuff 110 to receive oscillometric data for processing to determine a blood pressure of the patient. Processing circuitry 122, a pump 126 and a sensor 128 can be include with the NIBP monitor 120. The sensor 128 can be connected to the blood pressure cuff 110, such as by the tube 140, and can transmit sensor information to the processing circuitry 122 which can control the various functions and processing of the NIBP monitor 120.

The pump 126 can be connected to the inflatable bladder 113 of the blood pressure cuff 110 and the processing circuitry 122. The processing circuitry 122 can initiate the various functions of the pump, such a pressurizing the inflatable bladder 113 to a suitable and/or predetermined pressure to cause occlusion of a patient artery and the subsequent controlled deflation over a predetermined period of time. The pump 126 can draw a gas from a source, such as atmospheric air from the surrounding environment, and transmit the gas to the inflatable bladder 113, causing the bladder 113 to expand and exert a pressure on the portion of the patient about which the blood pressure cuff 110 is secured. As the inflatable bladder 113 is expanded by the incoming gas from the pump 126, it can contact the outer portion 114 which constrains the expansion of the inner portion 112. The inner portion 112 then expands to fill the volume, or void, between the outer portion 114 and the portion of the patient, causing the inner portion 112 to exert increasing pressure on the portion of the patient at the gas is pressurized within the inflatable bladder 113. Preferably, the pump 126 can achieve the suitable and/or predetermined pressure within the inflatable bladder 113 relatively quickly in order to begin the data acquisition process required to calculate the patient's blood pressure using the oscillometric method. The constraining of the inner portion 112 by the outer portion 114 can assist in reducing the time required to reach the suitable and/or predetermined pressure by reducing the volume in which the inner portion 112 is allowed to expand into. In a further embodiment, a manually actuated inflation mechanism can be used to inflate, pressurize and/or deflate the inflatable bladder 113 in a controlled manner. Reducing the amount of time spent on inflation and/or deflation of the cuff is critical when every second matters for emergency treatment of the patient. The additional time saved can be used to perform other high-value lifesaving treatment for the patient.

The pump 126 can include a pressure sensor to measure the pressure of the gas contained within the inflatable bladder 113. Alternatively, the sensor 128 can be used to monitor the pressure within the inflatable bladder 113. Once the pressure has reached a suitable and/or predetermined level, the processing circuitry 122 can stop the pump 126 and actuate a relief valve of the pump 126, or other controllable valve fluidically connected to the inflatable bladder 113, to cause the controlled release of pressure from the inflatable bladder 113 over the predetermined time duration.

The sensor 128 can be connected to and/or in fluid communication with the inner portion 112 of the blood pressure cuff 110 through the tube 140. The sensor 128 can be a number of suitable sensors/sensor systems for measuring a pressure within the inflatable bladder 113, such as a transducer 129. The transducer 129, due to the fluid communication through the tube 140, can sense and/or generate sensor data regarding the pressure of a gas, or other fluid, within the inflatable bladder 113. The data, or signals, from the transducer 129 can be transmitted to the processing circuitry 122 for processing and determining the blood pressure of the patient. The sensor 128 and/or the processing circuitry 122 can include one or more filters to assist with improving the quality of the signal transmitted from the sensor 128 and/or received by the processing circuitry 122.

By monitoring the pressure of the inflatable bladder, the transducer 129 can provide data to the processing circuitry 122 and/or pump 126 to control the inflation and deflation of the inflatable bladder 113. During deflation of the inflatable bladder, the cyclic pulsing of a patient artery causes the portion of the patient, about which the blood pressure cuff 110 is placed, to also pulse, decreasing the volume of the inflated inflatable bladder 113 and causing a momentary increase in the pressure of the inflatable bladder 113. These momentary pressure increases caused by the cyclic expansion of the patient artery can be detected by the transducer 129 and provides the oscillometric data for the processing circuitry to process to calculate a blood pressure of the patient.

The processing circuitry 122 can receive the oscillometric pressure data from the transducer and process the received data to calculate a patient's blood pressure. The processing circuitry 122 can include a noise reduction algorithm 124 that can be applied to the incoming signal and/or data from the transducer 129 to assist with removing noise. Noise in the incoming signal and/or data from the transducer 129 can affect the accuracy of the calculated blood pressure and/or can result in the signal and/or data being unusable in the calculation process.

The outer portion 114 of the blood pressure cuff 110 can assist with preventing noise from being introduced into the signal and/or data from the transducer 129 and the noise reduction algorithm 124 can further assist with removing additional noise from the signal and/or data. Additionally, the inclusion of the outer portion 114 can assist in isolating the sources of induced noise in the signal and/or data, allowing the noise reduction algorithm 124 to be targeted towards these other sources which can increase the efficacy of the noise reduction algorithm 124 in removing the noise from the signal and/or data.

Noise in the collected signal and/or data from the transducer 129 can be caused by a number of external influences, such as movement of the NIBP monitor 120, movement of the tube 140, movement of the blood pressure cuff 110 and/or other sources. The noise reduction algorithm 124 can be one or more sets of mathematical operations that can be applied to the incoming signal and/or data from the transducer 129 to assist with noise removal. The processing circuitry 122 can include one or more noise reduction algorithms 124 that can be selectively applied based on properties and/or characteristics of the incoming signal and/or data from the transducer 129. Additionally, the signal and/or data can be processed one or more times using the one or more noise reduction algorithms 124 to assist with increasing the quality of the signal and/or data through noise removal.

In testing, various sources of signal noise caused by motion were isolated and analyzed for their effect on the oscillometric signal. As discussed later, the sources of noise tested included movement/motion of/in the NIBP monitor 120, the tube 140 and the blood pressure cuff 110. Movement of/in these elements of the NIBP measurement system 100 were selected based on analysis of situations/conditions in which the NIBP measurement systems had reduced effectiveness, such as during patient transport. The testing indicated that movement of/in the blood pressure cuff 110 was the predominate cause of noise in the oscillometric signal and therefore reduction of such noise could have an effect on the efficacy and efficiency of the NIBP measurement system 100. Additionally, by addressing the noise induced by motion of the blood pressure cuff 110 directly through the application of an outer portion 114, the noise reduction algorithm 124 of the processing circuitry 122 can be directed to reduce or filter the noise caused by the other sources, such as movement of/in the NIBP monitor 120 and the tube 140. By studying the various sources of noise induction and their effect on the oscillometric signal, the noise reduction algorithm 124 can be further refined to filter the specific characteristics of the induced noise from the various sources.

The optional valve 130 can be connected in-line with the tube 140 or otherwise fluidically connected to the tube 140, such as by an auxiliary tube. The valve 130 can be positioned anywhere along the line 140 and can be within reach of a user of the NIBP measurement system 100 so that various elements of the system 100 can be accessed from a single user position. A user can actuate the valve 130 to release the pressure and/or gas from within the inflatable bladder. The valve 130 provides the user a more direct and quicker means of deflating the inflatable bladder 130. In emergency situations, the blood pressure cuff 110 may need to be quickly removed and/or repositioned, to do so the user can use the valve 130 to quickly deflate the inflatable bladder, if necessary, to allow for repositioning or removal of the blood pressure cuff 110 and make sure it is ready to begin another measurement cycle. Additionally, the valve 130 can be integrated with either of the blood pressure cuff 110 or the NIBP monitor 120 to allow the deflation of the inflatable bladder 113. The valve 130 can be a bleed valve in some examples or could be other types of valves that can release the pressure and/or gas, as desired.

For example, the valve 130 could be a bleed valve that is positioned in-line with a conventional 8' or 9' tube 140. The valve 130 is positioned near the cuff 110 so that a rescuer treating the patient can easily reach it during use, such as within 18"-2' away from the cuff 110 along the length of the tube 140. The example valve 130 can use various connectors to secure it in-line along the tube. Specifically, the valve 130 could use standard slip Luer and/or Luer lock connectors, barb fittings, quick disconnects, and any combination of these and other desired connectors. Different connectors could be used on opposing sides of the valve and in some examples one end of the valve is integrated into the tube and does not selectively detach from it while the opposing end of the valve has a releasable connector.

Figure 2A:
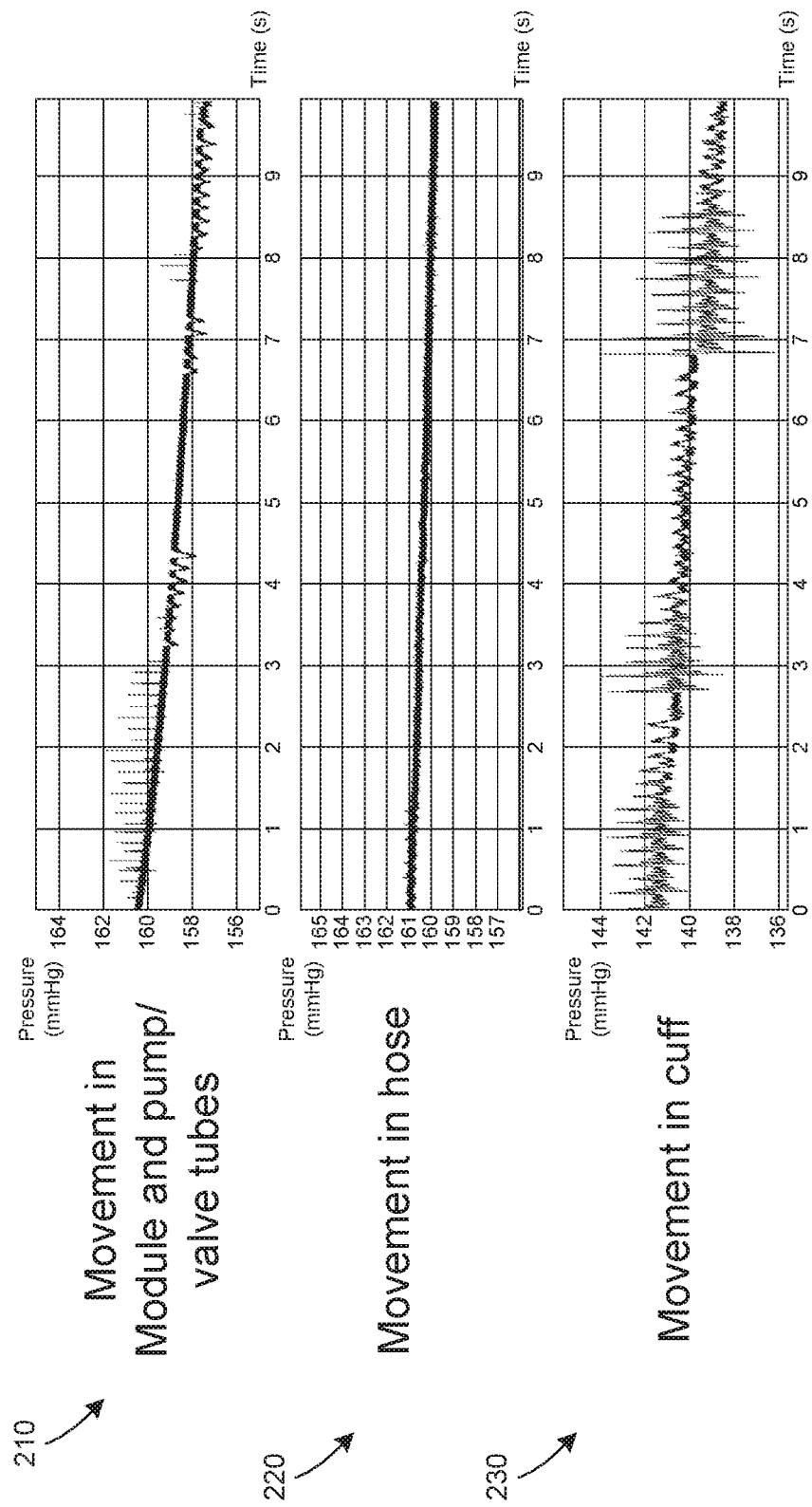
FIGS. 2A-2B are example oscillometric signals generated by a sensor of the non-invasive blood pressure measurement system.
Figure 2B:
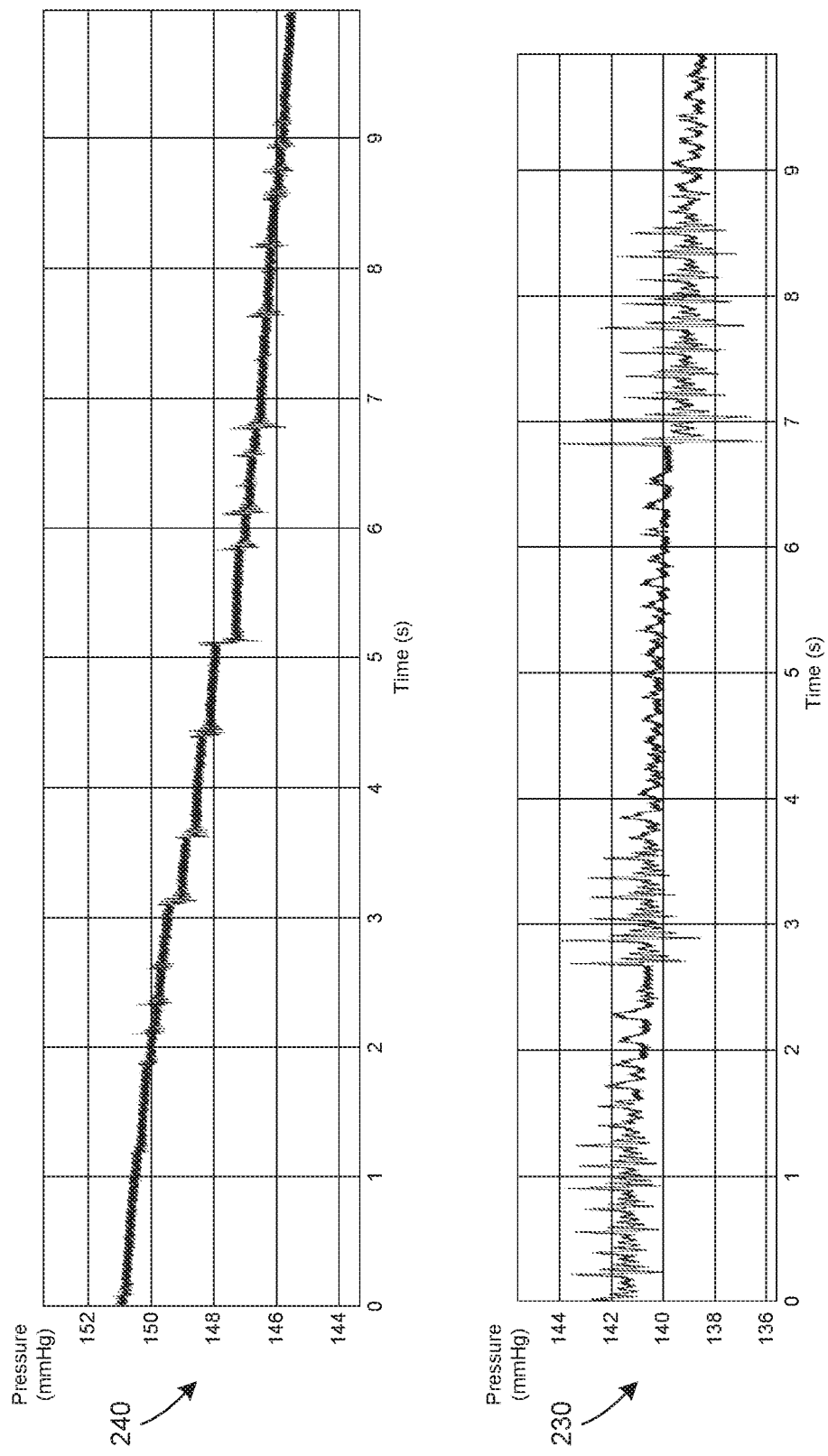

FIGS. 2A-2B are example oscillometric signals generated by a sensor of the non-invasive blood pressure measurement system. FIG. 2A illustrates example oscillometric signals with noise caused by isolated sources and FIG. 2B illustrates an example oscillometric signal having noise caused by a single noise source compared to signal influenced by the same noise source with the inclusion of the outer portion in the NIBP measurement system. In the example signal shown, the outer portion was a rigid shell constructed of polyvinyl chloride (PVC).

FIG. 2A illustrates the effects the various individual noise sources have on the oscillometric signal captured at the pressure transducer. In the experimental testing illustrated in the plots 210, 220 and 230, a blood pressure cuff was fastened about a hard mandrel and inflated and the NIBP measurement process was performed. The blood pressure cuff was slowly deflated over a predetermined period of time and the signal from the pressure transducer, indicative of the pressure of the blood pressure cuff, was captured and plotted as shown. In each of the experiments, motion of a specific component of the NIBP measurement system was assessed. For each experiment one element of the NIBP measurement system was subjected to external stimuli while the remaining elements were not, to generate an oscillometric signal having predominately a single noise source as caused by the external stimuli on the particular element of the NIBP measurement system. The external stimuli applied was representative of external stimuli the NIBP measurement system would be expected to experience during use, i.e. movement of/in the various components of the system. Additionally, the motion of the components induces low frequency noise, which is typically within the band of error of the noise reduction algorithm. As such, removal of the induced low frequency noise by the noise reduction algorithm can be ineffective. In the example experimental plots shown, the external stimuli were limited to a single stimulus simulated by repeated tapping of the element to cause motion of and/or within the element being subjected to the external stimuli.

Plot 210 shows the oscillometric signal as it is effected by the isolated movement of/in NIBP monitor as caused by an external stimulus, with no deliberate application of an external stimulus on the other elements of the NIBP measurement system. Similarly, plot 220 shows substantially the same oscillometric signal as effected by the isolated movement of/in the hose, such as the tube 140 of FIG. 1, connecting the NIBP monitor and the cuff, as caused by an external stimulus. Also similarly, plot 230 shows substantially the same oscillometric signal as effected by the isolated movement of/in the cuff, such as the blood pressure cuff 110 of FIG. 1. As illustrated by the plots 210, 220 and 230, the principal variable in introducing noise into the captured oscillometric signal is through movement of the cuff. In a hospital setting, where a patient is confined primarily to a bed, motion of the cuff is typically minimal. In a transport or trauma treatment at a point-of-care situation, with the induced motion caused by the transport vehicle and its travel or uncontrolled patient movement, respectively, movement of the cuff is likely and expected. In such a situation, cuff motion induced noise can be expected to adversely impact the acquisition of a blood pressure measurement using an NIBP measurement system. As such, the use of an outer portion, such as the tested rigid, PVC shell, to reduce the influence of external stimuli on the captured oscillometric signal can increase the efficacy and/or efficiency of determining a patient's blood pressure using an NIBP measurement system.

FIG. 2B illustrates the example plot 230, showing the oscillometric signal having noise caused by movement of the cuff, and example plot 240, showing substantially the same oscillometric signal with the cuff protected by an outer portion to reduce the noise introduced into the oscillometric signal. As can be seen by the example plots 230 and 240, there is significant reduction in the amount of noise present in the oscillometric signal when the cuff is surrounded by an outer portion that reduces the external stimuli transmitted through the cuff and into the oscillometric signal.

Figure 3A:
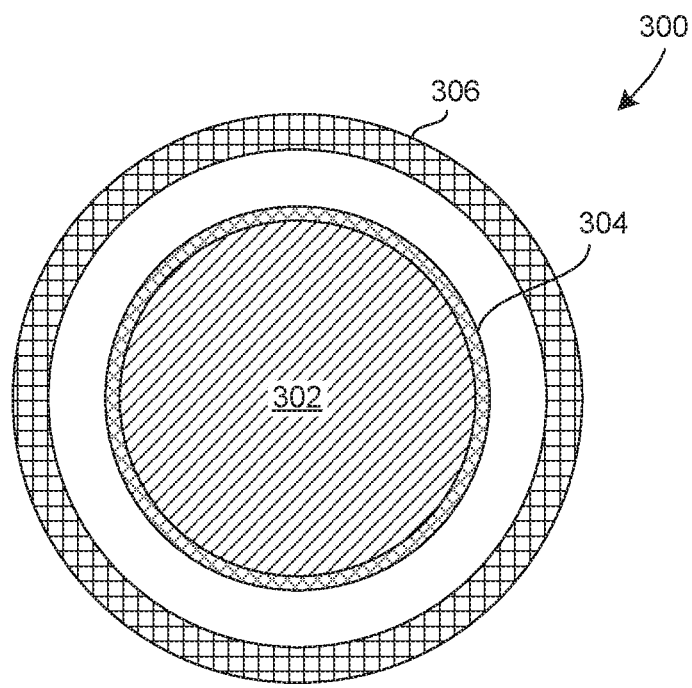
FIGS. 3A-3B are cross-sectional views of an example blood pressure cuff for use with a non-invasive blood pressure measurement system.
Figure 3B:
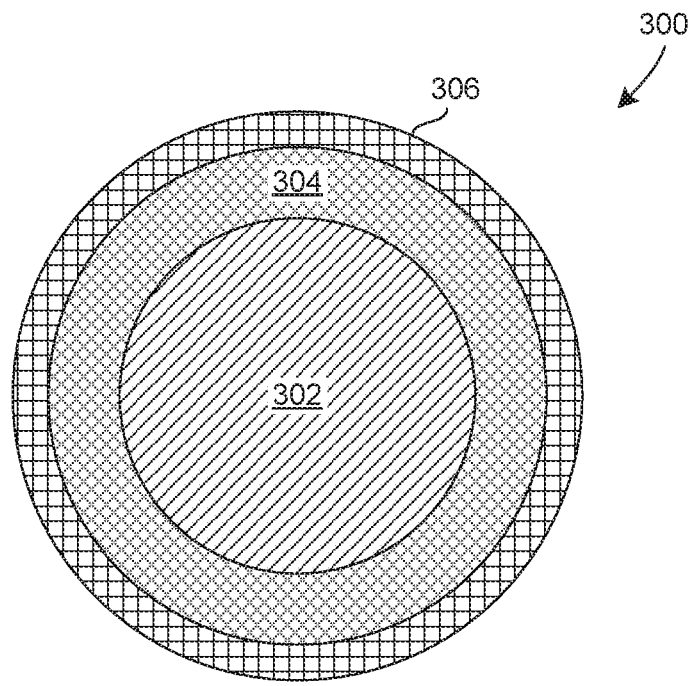

FIGS. 3A-3B are cross-sectional views of an example blood pressure cuff for use with a non-invasive blood pressure measurement system. FIGS. 3A-3B show the example blood pressure cuff 300 about a portion of a patient, such as an arm 302. The blood pressure cuff 300 includes an inner portion 304 that is inflatable or includes an inflatable portion, such as an inflatable bladder, and an outer portion 306 that is rigid or semi-rigid. In FIG. 3A, the inner portion 304 is shown deflated about the arm 302 and in FIG. 3B, the inner portion 304 is shown inflated, or expanded, to contact and exert pressure on both the arm 302 and the outer portion 306. The outer portion 306, as discussed previously, restricts the volume into which the inner portion 304 is allowed to expand. This restricted, or reduced, volume can assist with achieving the suitable and/or predetermined pressure within the inner portion 304 to occlude an artery of the arm 302.

The inner portion 304 and the outer portion 306 can be separate elements, selectively attachable or integrated into a single unit. As separate elements, the inner portion 304 and outer portion 306 are separate elements that can be affixed to, or placed about, a portion of a patient. The inner portion 304 and/or outer portion 306 can include features and/or elements that can restrict motion between the two elements 304, 306. As selectively attachable elements, the two portions 304 and 306 are separate elements that can be selectively joined together, such as prior to being placed about the portion of the patient or being placed separately about the portion of the patient and coupled together. In an example embodiment, the inner portion 304 can include a loop portion of a hook-and-loop fastener about its exterior and the outer portion 306 can include the corresponding hook portion about an interior, such that when the inner portion 304 and outer portion 306 are placed against together, the hook and loop portions engage to selectively couple the portions 304 and 306 together. The inner 304 and outer 306 portions can be selectively uncoupled by pulling the two portions apart to disengage the hook-and-loop fastener(s). As integrated elements, the inner portion 304 and outer portion 306 are inseparable, such as being permanently affixed to each other or formed as a single unit during a manufacturing process.

FIGS. 4A-4D illustrate example embodiments of an outer portions 400a-400d for use with NIBP measurement system. The various outer portions can be separate from the inner portion, or an inflatable portion, of a blood pressure cuff or can be integrated with to form a single blood pressure cuff unit. Additionally, the various outer portions can be used in conjunction with a standard inflatable blood pressure cuff, which allows existing inflatable cuff systems to be retrofit with the new outer portion(s) disclosed here.

While the example outer portions 400a-400d are shown as having smooth, uninterrupted surfaces, various features, reliefs and/or openings can be included on the outer portions 400a-400d for a variety of purposes and/or requirements related to use, storage and/or manufacturing of the outer portions 400a-400d. For example, openings and or reliefs can be formed in the surfaces of the outer portions 400a-400d to reduce the weight of outer portion 400a-400d and/or to reduce an amount of material used to form the outer portion 400a-400d. Further, each of the outer portions 400a-400d can be rigid or semi-rigid in nature and can further be collapsible or not. Additionally, various other portions, systems and/or components of the NIBP measurement system can be integrated and/or attached to the outer portion 400a-400d.

Figure 4A:
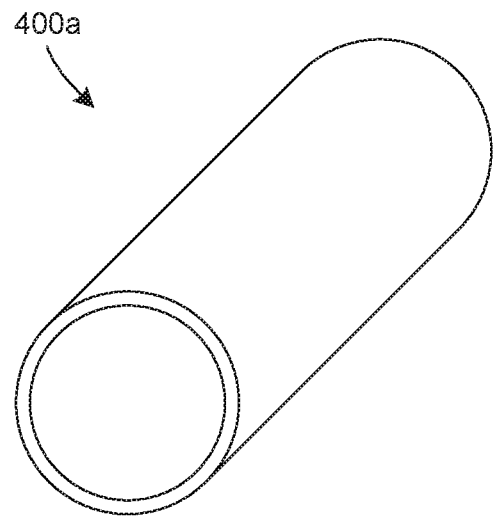
FIGS. 4A-4D are example outer portions for use with a non-invasive blood pressure measurement system.

In FIG. 4A, the outer portion 400a is shown as substantially a single unit which can be slid, or otherwise placed, about the inner portion. Using the example outer portion 400a, the inner, or inflatable portion, of the blood pressure cuff can be secured about a portion of the patient, such as their arm, and then the outer portion 400a can be slid over the portion of the patient and the inner portion of the blood pressure cuff. The outer portion 400a can be secured, such as to the patient and/or the inner portion, to restrict movement of the outer portion 400a relative to the inner portion.

Figure 4B:
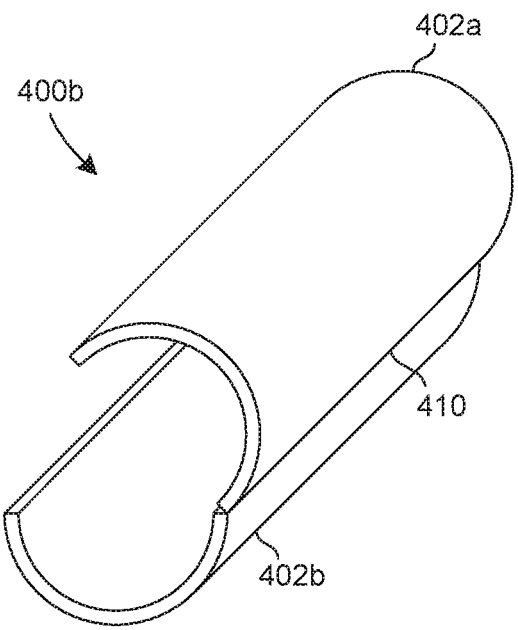

In FIG. 4B, the outer portion 400b is shown as a single unit having an upper portion 402a and a lower portion 402b, joined together along a first edge or portion, such as at 410. The upper portion 402a and lower portion 402b are separable along at least a second edge to allow the outer portion 400b to be placed about a portion of the patient and the inner portion of the blood pressure cuff. Once placed about the patient and inner portion, the two portions, 402a and 402b can then be secured together prior to beginning the NIBP measurement process. Various securing means, such as latches, snaps, locks, straps, belts and other can be used to secure or fasten the two portions 402a and 402b. The securing element(s) can be adjustable to account for differently sized portions of patients. The joint 410 between the two portions 402a and 402b can be a hinge or other means of securing the two portions 402a and 402b together along at least an edge while allowing the two portions 402a and 402b to be separable along at least an edge so that the outer portion 400b can be placed about a portion of a patient. The securing element(s) can be positioned along the separable edge of the outer portion 400b, allowing the separable edge to be secured and closed during use of the outer portion 400b.

Figure 4C:
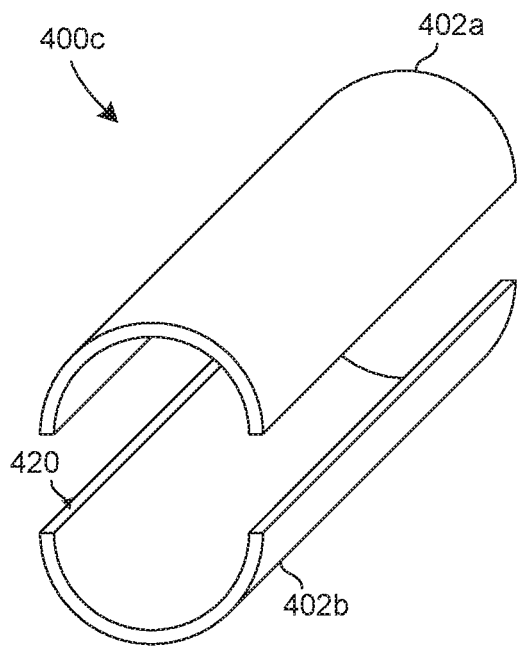

In FIG. 4C, the outer portion 400c is shown as two independent, separable portions, including a top portion 402a and bottom portion 402b. To secure the outer portion 400c about a portion of a patient, and the inner portion of the blood pressure cuff, various external securement means, such as latches, snaps, locks, straps, belts and other can be used to secure or fasten the two portions 402a and 402b together. Alternatively, or additionally, the mating surface 420 of the upper portion 402a and/or lower portion 402b can include features to align, interlock and/or secure the upper portion 402a and lower portion 402b together about the portion of the patient. Such feature can include protrusions formed on one of the portions 402a, 402b that interface with corresponding slots formed in the other portion. Additionally, one or more of the various described means of securing and/or fastening the portions 402a, 402b together can be used to secure the outer portion 400c about the inner portion of the blood pressure cuff.

Figure 4D:
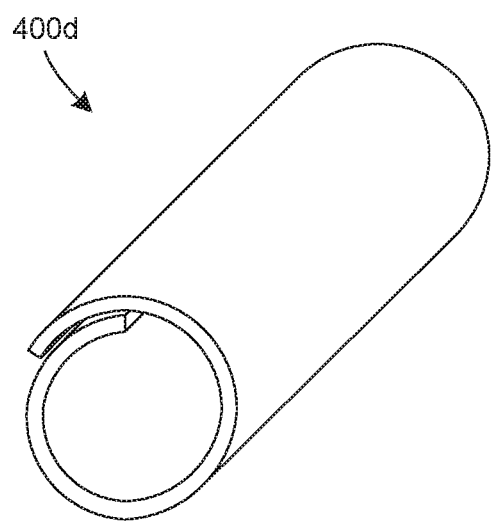

In FIG. 4D, the outer portion 400d is shown as having an overlapping portion. The overlapping nature of the outer portion 400d can allow the outer portion 400d to have a varying circumference to fit about a variety of inner portions and/or patients. Various securing means can be releasably or permanently affixed/integrated with the outer portion 400d to assist with securing the outer portion 400d to a desired and/or required circumference. The outer portion 400d can include inner features and/or surface treatments to assist with securing the outer portion 400d to the inner portion about which the outer portion 400d is placed.

In another embodiment in which the outer portion is a semi-rigid shell, the outer portion can be formed of multiple elements that can be assembled prior to use. For example, the outer portion can include a flexible portion made of a fabric having a pocket(s) or sleeve(s) disposed thereon. Prior to use, one or more rigid elements can be placed within the pocket(s)/sleeve(s) to provide a structure to the fabric portion, thereby forming a semi-rigid outer portion. The rigid elements can be removable or integrated with the fabric portion to form the semi-rigid outer shell. As with the previously described outer portions of FIGS. 4A-4D, the semi-rigid outer portion can be single element that is placed about the inner portion, a single element separable along a portion to assist with placing the outer semi-rigid portion about the inner portion, or a multi-piece construction that can be placed and/or secured together.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

The invention claimed is:

1. A non-invasive blood pressure measurement system, comprising:
    an inflatable bladder configured to wrap around a circumference of an arm;
    a rigid shell disposed around the inflatable bladder and configured to restrict radial expansion of the inflatable bladder when the inflatable bladder inflates, the rigid shell comprising a lattice structure wherein openings radially extend through the rigid shell such that the openings are spaced apart along the rigid shell at intervals;
    a transducer configured to detect a pressure in the inflatable bladder over time; and
    a processor configured to detect a blood pressure by analyzing the pressure in the inflatable bladder over time.

2. The non-invasive blood pressure measurement system of claim 1, wherein the rigid shell comprises a tube.

3. The non-invasive blood pressure measurement system of claim 1, wherein the rigid shell further comprises:
    a first portion;
    a second portion; and
    a hinge connected to an edge of the first portion and an edge of the second portion.

4. The non-invasive blood pressure measurement system of claim 1, wherein the rigid shell comprises two separable portions.

5. The non-invasive blood pressure measurement system of claim 1, further comprising: a valve coupled between the inflatable bladder and the transducer and in fluid communication with the inflatable bladder, the valve being configured to release the pressure in the inflatable bladder.

6. The non-invasive blood pressure measurement system of claim 1, wherein the rigid shell comprises polyvinyl chloride (PVC) or fiberglass.

7. The non-invasive blood pressure measurement system of claim 1, wherein a first portion of the rigid shell overlaps a second portion of the rigid shell in a radial direction.

8. A non-invasive blood pressure measurement system, comprising:
    a cuff comprising:
        an inflatable bladder configured to be radially disposed around a circumference of an arm; and
        a rigid shell radially disposed around the inflatable bladder and configured to restrict radial expansion of the inflatable bladder when the inflatable bladder inflates, the rigid shell comprises a lattice structure wherein openings radially extend through the rigid shell such that the openings are spaced apart along the rigid shell at intervals;

a sensor coupled to the cuff and configured to generate a signal indicative of a pressure in the inflatable bladder over time; and a non-invasive blood pressure monitor, including:
  a pump in fluid communication with the inflatable bladder, and
  a processor configured to:
    filter the signal; and
    determine a blood pressure by analyzing the filtered signal.

9. The non-invasive blood pressure measurement system of claim 8, wherein the rigid shell comprises elements that are coupled together.

10. The non-invasive blood pressure measurement system of claim 8, wherein the rigid shell further comprises:
  a first portion;
  a second portion; and
  a hinge connected to an edge of the first portion and an edge of the second portion.

11. The non-invasive blood pressure measurement system of claim 8, wherein the rigid shell comprises polyvinyl chloride (PVC) or fiberglass.

12. The non-invasive blood pressure measurement system of claim 8, wherein a first portion of the rigid shell overlaps a second portion of the rigid shell in a radial direction.

13. A device, comprising:
  a rigid shell configured to be radially disposed around a circumference of an arm, the rigid shell comprises a lattice structure wherein openings radially extend through the rigid shell such that the openings are spaced apart along the rigid shell at intervals;
  an inflatable bladder configured to be disposed around the circumference of the arm and to selectively inflate between the arm and the rigid shell; and
  a sensor configured to detect a pressure in the inflatable bladder over time, the pressure in the inflatable bladder over time being indicative of a blood pressure.

14. The device of claim 13, further comprising:
  a pump configured to increase the pressure in the inflatable bladder; and
  a valve configured to release the pressure in the inflatable bladder.

15. The device of claim 13, wherein the rigid shell comprises a tube.

16. The device of claim 13, wherein the rigid shell further comprises:
  a first portion;
  a second portion; and
  a hinge connected to an edge of the first portion and an edge of the second portion.

17. The device of claim 16, wherein the rigid shell further comprises a securing element configured to secure the first portion and the second portion together, the securing element comprising a latch, a snap, a lock, a strap, or a belt.

18. The device of claim 13, wherein the rigid shell comprises polyvinyl chloride (PVC) or fiberglass.

19. The device of claim 13, wherein the rigid shell is affixed to the inflatable bladder.

20. The device of claim 13, wherein an adjustable first portion of the rigid shell is configured to overlap an adjustable second portion of the rigid shell in a radial direction.

* * * * *